United States Patent
Zhou (10) Patent No.: US 10,894,815 B2
(45) Date of Patent: *Jan. 19, 2021

(54) COMPOSITIONS AND METHODS FOR TREATING HEART FAILURE IN DIABETIC PATIENTS (71) Applicant: Zensun (Shanghai) Science & Technology, Co., Ltd., Shanghai (CN)

(72) Inventor: Mingdong Zhou, Shanghai (CN)

(73) Assignee: Zensun (Shanghai) Science & Technology, Co., Ltd., Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 14/429,750

(22) PCT Filed: Oct. 8, 2012

(86) PCT No.: PCT/CN2012/001353
§ 371 (c)(1),
(2) Date: Mar. 19, 2015

(87) PCT Pub. No.: WO2014/056121
PCT Pub. Date: Apr. 17, 2014

(65) Prior Publication Data
US 2015/0284440 A1    Oct. 8, 2015

(51) Int. Cl.
*A61K 38/16* (2006.01)
*A61K 38/18* (2006.01)
*C07K 14/475* (2006.01)

(52) U.S. Cl.
CPC ...... *C07K 14/4756* (2013.01); *A61K 38/1883* (2013.01)

(58) Field of Classification Search
None
See application file for complete search history.

(56) References Cited

U.S. PATENT DOCUMENTS

| | | | |
|---|---|---|---|
| 5,530,109 A | 6/1996 | Goodearl et al. | |
| 5,686,102 A | 11/1997 | Gross et al. | |
| 5,716,930 A | 2/1998 | Goodearl et al. | |
| 5,736,154 A | 4/1998 | Fuisz | |
| 5,741,511 A | 4/1998 | Lee et al. | |
| 5,834,229 A | 11/1998 | Vandlen et al. | |
| 5,886,039 A | 3/1999 | Kock et al. | |
| 5,941,868 A | 8/1999 | Kaplan et al. | |
| 6,197,801 B1 | 3/2001 | Lin | |
| 6,258,374 B1 | 7/2001 | Friess et al. | |
| 7,226,907 B1 | 6/2007 | Zhou | |
| 7,612,164 B2 | 11/2009 | Zhou | |
| 7,795,212 B2 | 9/2010 | Zhou | |
| 7,964,555 B2 | 6/2011 | Zhou | |
| 8,476,405 B2 | 7/2013 | Zhou | |
| 8,609,620 B2 | 12/2013 | Zhou | |
| 8,785,387 B2 | 7/2014 | Zhou | |
| 9,012,400 B2 | 4/2015 | Zhou | |
| 9,089,524 B2 | 7/2015 | Zhou | |
| 9,340,597 B2 | 5/2016 | Zhou | |
| 9,434,777 B2 | 9/2016 | Zhou | |
| 9,555,076 B2 | 1/2017 | Zhou | |
| 9,580,515 B2 | 2/2017 | Zhou | |
| 9,592,339 B2 | 3/2017 | Zhou | |
| 9,655,949 B2 | 5/2017 | Zhou | |
| 2006/0199767 A1 | 9/2006 | Zhou | |
| 2007/0129296 A1 | 6/2007 | Zhou | |
| 2007/0190127 A1 | 8/2007 | Zhou | |
| 2007/0213264 A1 | 9/2007 | Zhou | |
| 2009/0156488 A1 | 6/2009 | Zhou | |
| 2011/0229444 A1 | 9/2011 | Zhou | |
| 2011/0236477 A1 | 9/2011 | Schneider et al. | |
| 2013/0078235 A1 | 3/2013 | Zhou | |
| 2014/0364366 A1 | 12/2014 | Zhou | |
| 2016/0089329 A1 | 3/2016 | Zhou | |
| 2016/0095903 A1 | 4/2016 | Zhou | |
| 2016/0297859 A1 | 10/2016 | Zhou | |
| 2016/0324876 A1 | 11/2016 | Zhou | |
| 2017/0007671 A1 | 1/2017 | Zhou | |
| 2017/0189489 A1 | 7/2017 | Zhou | |
| 2017/0232068 A1 | 8/2017 | Zhou | |
| 2017/0313784 A1 | 11/2017 | Zhou | |
| 2017/0326204 A1 | 11/2017 | Zhou | |
| 2017/0360889 A1 | 12/2017 | Zhou | |
| 2017/0368140 A1 | 12/2017 | Zhou | |
| 2018/0104311 A1 | 4/2018 | Zhou | |
| 2018/0133291 A1 | 5/2018 | Zhou | |

FOREIGN PATENT DOCUMENTS

| | | |
|---|---|---|
| WO | WO 97/09425 A1 | 3/1997 |
| WO | WO 00/37095 A1 | 6/2000 |
| WO | WO 00/64400 A2 | 11/2000 |

(Continued)

OTHER PUBLICATIONS

Li et al. (2011). Cardiovascular Diabetology. 10:69., pp. 1-8.*
Carraway et al., "Neuregulin-2, a new ligand of ErbB/ErbB4-receptor tyrosine kinase," *Nature*, 387:512-516 (1997).
Chang et al., "Ligands for ErbB-family receptors encoded by a neuregulin-like gene," *Nature*, 387:509-512 (1997).
Corfas et al., "Neuregulin 1-erbB signaling and the molecular/cellular basis of schizophrenia," *Nature Neuroscience*, 7(6):575-580 (2004).

(Continued)

*Primary Examiner* — Christine J Saoud
*Assistant Examiner* — Jon M Lockard
(74) *Attorney, Agent, or Firm* — Jones Day (57) ABSTRACT

The present invention provides the use of neuregulin protein for the preparation of medication for preventing, treating or delaying heart failure in humans and methods for preventing, treating or delaying heart failure in humans using said medication.

9 Claims, 1 Drawing Sheet
Specification includes a Sequence Listing.

(56) References Cited

FOREIGN PATENT DOCUMENTS

| WO | WO 00/78347 A1 | 12/2000 | |
|---|---|---|---|
| WO | WO 03/099300 A1 | 12/2003 | |
| WO | WO 03/099320 A1 | 12/2003 | |
| WO | WO 03/099321 A1 | 12/2003 | |
| WO | WO 2007/062594 A1 | 6/2007 | |
| WO | WO 2007/076701 A1 | 7/2007 | |
| WO | WO 2008/028405 A1 | 3/2008 | |
| WO | WO 2009/033373 A1 | 3/2009 | |
| WO | WO 2010/060265 A1 | 6/2010 | |
| WO | WO 2010/060266 A1 | 6/2010 | |
| WO | WO 2010/142141 A1 | 12/2010 | |
| WO | WO 2010142141 A1 * | 12/2010 | ......... A61K 38/1883 |
| WO | WO 2011/011388 A2 | 1/2011 | |
| WO | WO 2011/091723 A1 | 8/2011 | |
| WO | WO 2013/053076 A1 | 4/2013 | |
| WO | WO 2013/053158 A1 | 4/2013 | |
| WO | WO 2013/053201 A1 | 4/2013 | |
| WO | WO 2014/056121 A1 | 4/2014 | |
| WO | WO 2014/187342 A1 | 11/2014 | |
| WO | WO 2015/101182 A1 | 7/2015 | |
| WO | WO 2015/101208 A1 | 7/2015 | |
| WO | WO 2016/045493 A1 | 3/2016 | |
| WO | WO 2016/058493 A1 | 4/2016 | |

OTHER PUBLICATIONS

Database Biosis, "Deficient cardiac neuregulin-ErbB signaling in type 2 diabetes, and beneficial effects of treatment with neuregulin-1," Database accession No. PREV201000179850, Nov. 2009 (2 pages).

Higashiyama et al., "A novel brain-derived member of the epidermal growth factor family that interacts with ErbB3 and ErbB4," *J Biochem.*, 122:675-680 (1997).

Hijazi et al., "NRG-3 in human breast cancers: activation of multiple erbB family proteins," *Int. J. Oncol.*, 13:1061-1067 (1998).

Holmes et al., "Identification of heregulin, a specific activator of p185$^{erbB2}$," *Science*, 256:1205-1210 (1992).

Huang et al., "Effects of neuregulin-1 on ventricular remolding in experimental diabetic cardiomyopathy," *Chinese Pharmacological Bulletin*, 27(11):1532-1536 (2011) (English abstract).

Huang, "Experimental study of the NRG-1 treatment in diabetic cardiomyopathy rats," Chinese Master's Theses Full-text Database Medicine and Health Sciences, Feb. 2, 2012, No. 4, E065-60 (English abstract).

Li et al., "Therapeutic effects of neuregulin-1 in diabetic cardiomyopathy rats," Cardiovascular Diabetolgoy, 10(0:69, pp. 1-8 (2011).

Sadick et al., "Analysis of heregulin-induced ErbB2 phosphorylation with a high-throughput kinase receptor activation enzyme-linked immunosorbant assay," *Anal. Biochem.*, 235:207-214 (1996).

Watson et al., *Molecular Biology of the Gene*, 4$^{th}$ Edition, The Bejacmin/Cummings Publishing Company, Inc., Menlo Park, CA, p. 224 (1987).

Kida et al., "Congestive heart failure in type 2 diabetes—clinical features, risk factors, characterization of cardiac function, and survival prognosis," *J Japan Diab. Soc.*, 44(11):887-894 (2001). English abstract attached.

Doggen et al., "Deficient cardiac neuregulin-ErbB signaling in type 2 diabetes, and beneficial effects of treatment with neuregulin-1," *Circulation*, 82$^{nd}$ Scientific Session of the American-Heart Association, Orlando, Florida, Nov. 13-18, 2009, 120(18, Suppl. 2):S828 (2009).

* cited by examiner

SEQUENCE LISTING

<160> NUMBER OF SEQ ID NOS: 2

<210> SEQ ID NO 1
<211> LENGTH: 61
<212> TYPE: PRT
<213> ORGANISM: Homo sapiens

<400> SEQUENCE: 1

```
Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln
    50                  55                  60
```

<210> SEQ ID NO 2
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

```
Ala Glu Lys Glu Lys Thr Phe Cys Val Asn Gly Gly Glu Cys Phe Met
1               5                   10                  15

Val Lys Asp Leu Ser Asn Pro
            20
```

COMPOSITIONS AND METHODS FOR TREATING HEART FAILURE IN DIABETIC PATIENTS

This application is a U.S. national stage application of PCT/CN2012/001353, having an international filing date of Oct. 8, 2012, the entire contents of which are incorporated herein by reference.

Incorporated herein by reference is the Sequence Listing being concurrently submitted via EFS-Web as an ASCII text file named 11748-048-999_Sequence_Listing.txt, created Mar. 19, 2015, and being 851 bytes in size.

FIELD OF THE INVENTION

The present invention relates to the use of neuregulin protein for the preparation of medication for preventing, treating or delaying heart failure in humans and methods for preventing, treating or delaying heart failure in humans using said medication. Particularly, the present invention provides methods for preventing, treating or delaying heart failure using the composition comprising a neuregulin protein in diabetic patients who has had or at high risk of a complication of heart diseases.

BACKGROUND OF THE INVENTION

Over recent years, the prevalence of diabetes mellitus (DM), in particular type 2 diabetes, has increased significantly. New figures indicate that the number of people living with diabetes is expected to rise from 366 million in 2011 to 552 million by 2030, if no urgent action is taken. The major cause of morbidity and mortality in diabetic patients is cardiac complications or cardiovascular disease, particularly coronary heart disease (CHD), which accounts for as much as 75% of deaths in people with type 2 DM. While the most common cardiac manifestation in diabetic patients is CHD, DM also appears to be strongly linked to HF which can be progressed from CHD. Approximately 15 to 25% of patients with HF are diabetics. Thus lots of people with diabetic suffer from cardiac complications especially HF.

DM may be causally related to cardiac complications especially HF development by the following mechanisms: due to associated comorbidities, by favoring the development of coronary atherosclerosis, impaired calcium handling or through a specific diabetic cardiomyopathy and so on.

Associated comorbidities or risk factors may partly account for the increased risk of HF in diabetic patients. These cardiovascular risk factors such as dyslipidaemia, hypertension, hypercoagulability, obesity and inflammation are part of the insulin resistance syndrome and are, at least partly, regulated by nuclear peroxisome proliferator-activated receptors (PPARs); activation of PPAR-gamma improve insulin sensitivity and endothelial function, and lower inflammation and blood pressure. In the Framingham cohort, diabetic men and women had higher blood pressures and were more obese than non-diabetics. The same observation has been reported in HF populations.

The increased risk of atherosclerosis in diabetic patients may also contribute significantly to the increased risk of HF. DM is associated with a markedly increased risk of coronary artery disease which is the underlying cause of HF. Hyperglycemia induces a large number of alterations in vascular tissue that potentially promote accelerated atherosclerosis.

High prevalence of isolated diastolic dysfunction among diabetic patients had been observed. It may be resulted from impaired calcium handling in diabetic patients. In a chronic model of diabetes, depressed sarcoplasmic reticulum (SR) $Ca^{2+}$ reuptake during the relaxation phase of cardiac myocytes, which was associated with prolonged action potentials (APs) and after depolarizations at the cellular level and with impaired ventricular relaxation at the organ level. These mechanisms of impaired SR $Ca^{2+}$ uptake appear to underlie isolated subclinical diastolic dysfunction, an early pathological event that may progress to diastolic heart failure.

There are also data to suggest that DM may predispose to HF development through the existence of a specific diabetic cardiomyopathy. The exact mechanism(s) by which DM may induce HF independent of epicardial coronary artery disease is (are) unknown but several hypotheses have been advanced: these include microangiopathy, metabolic factors, and fibrosis.

Otherwise, the renin-angiotensin system is unregulated with diabetes, and Angiotensin II (Mg II) locally may lead to oxidative damage, activating cardiac cell death. Diabetes was characterized by an 85-fold, 61-fold, and 26-fold increase in apoptosis of myocytes, endothelial cells, and fibroblasts, respectively. Moreover, diabetes and hypertension increased necrosis in myocytes and endothelial cells. Apoptosis and necrosis of myocytes may contribute to the development of a dilated myopathy which may result in heart failure.

One promising new therapy involves administration of neuregulin (hereinafter referred to as "NRG") to a patient suffering from or at risk of developing cardiac complications especially heart failure. Neuregulin may prevent, treat or delay cardiac complications in diabetic patients with its functions in improving myocardial structure, promoting survival of cardiomyocytes, promoting calcium homeostasis and its anti-atherosclerosis effect which are damaged in diabetic patients.

NRGs, a family of EGF-like growth factors, comprises a family of structurally related growth and differentiation factors that include NRG1, NRG2, NRG3 and NRG4 and isoforms thereof, are involved in an array of biological responses: stimulation of breast cancer cell differentiation and secretion of milk proteins; induction of neural crest cell differentiation to Schwann cells; stimulation of skeletal muscle cell synthesis of acetylcholine receptors; and, promotion of myocardial cell survival and DNA synthesis. In vivo studies of neuregulin gene-targeted homozygous mouse embryos with severe defects in ventricular trabeculae formation and dorsal root ganglia development indicate that neuregulin is essential for heart and neural development.

NRGs bind to the EGF receptor family, which comprises EGFR, ErbB2, ErbB3 and ErbB4, each of which plays an important role in multiple cellular functions, including cell growth, differentiation and survival. They are protein tyrosine kinase receptors, consisting of an extracellular ligand-binding domain, transmembrane kinase domain and cytoplasmic tyrosine kinase domain. After NRG bind to the extracellular domain of ErbB3 or ErbB4, it induces a conformational change that leads to heterodimer formation between ErbB3, ErbB4 and ErbB2 or homodimer formation between ErbB4 itself, which results in phosphorylation of the receptor's C-terminal domain inside the cell membrane. The phosphorylated intracellular domain then binds additional signal proteins inside the cell, activating the corresponding downstream AKT or ERK signaling pathway, and inducing a series of cell reactions, such as stimulation or depression of cell proliferation, cell differentiation, cell apoptosis, cell migration or cell adhesion. Among these receptors, mainly ErbB2 and ErbB4 are expressed in the heart.

It has been shown that the EGF-like domains of NRG-1, ranging in size from 50 to 64-amino acids, are sufficient to bind to and activate these receptors. Previous studies have shown that neuregulin-1β (NRG-1β) can bind directly to ErbB3 and ErbB4 with high affinity. The orphan receptor, ErbB2, can form heterodimer with ErbB3 and ErbB4 with higher affinity than ErbB3 or ErbB4 homodimers. Research in neural development has indicated that the formation of the sympathetic nervous system requires an intact NRG-1β, ErbB2 and ErbB3 signaling system. Targeted disruption of the NRG-1β or ErbB2 or ErbB4 led to embryonic lethality due to cardiac development defects. Recent studies also highlighted the roles of NRG-1β, ErbB2 and ErbB4 in the cardiovascular development as well as in the maintenance of adult normal heart function. NRG-1β has been shown to enhance sarcomere organization in adult cardiomyocytes. The administration of a recombinant NRG-1β EGF-like domain significantly improves or protects against deterioration in myocardial performance in distinct animal models of heart failure as well as in clinical trials. These results make NRG-1 promising as a lead compound for the treatment of heart failure. And from the disclosure of this application, we have provided more evidences that NRG-1 treatment can provide preventive or therapeutic benefits to the diabetic patients who has had or at high risk of a complication of heart diseases.

SUMMARY OF THE INVENTION

In human clinical trials of neuregulin for treating heart failure, applicant discovered that heart failure patients who are diabetic patients will receive significant benefits from neuregulin treatment. Such benefits include significant reduction in mortality rate.

It has been discovered by applicant that NRG enhances cardiac muscle cell differentiation and organization of sarcomeric and cytoskeleton structure, as well as cell adhesion. It has been also discovered by applicant that NRG significantly improves or protects against deterioration in myocardial performance in distinct animal models of heart failure and in clinical trials. NRG is effective in improving myocardial structure, promoting survival of cardiomyocytes, promoting calcium homeostasis and its anti-atherosclerosis effect which are damaged in diabetic patients. Neuregulin, neuregulin polypeptide, neuregulin derivatives, or compounds which mimic the activities of neuregulins, fall within the scope of the present invention.

Thus, in a first aspect of the present invention, a method is provided for preventing, treating or delaying cardiac complications in diabetic patients, which comprises administering a pharmaceutical composition comprising an effective amount of neuregulin to the patients. In some embodiments, the cardiac complication is heart failure. In some embodiments, the pharmaceutical composition is administered to the patients intravenously or subcutaneously. In some embodiments, the pharmaceutical composition is administered to the patients for an introduction regimen. In some optimized embodiments, the introduction regimen includes continuous administration of the pharmaceutical composition for at least 3, 5, 7 or 10 days. In some better embodiments, the pharmaceutical composition is administered to the patients for a maintenance regimen for at least 6 months after the introduction. In some better embodiments, the maintenance regimen includes an administration of the pharmaceutical composition every 3, 5, 7 or 10 days.

In a second aspect, a method is provided for preventing, treating or delaying hear failure, which comprises administering a pharmaceutical composition comprising an effective amount of neuregulin to the patients. In some embodiments, the patients are diabetic patients. In some embodiments, the pharmaceutical composition is administered to the patients intravenously or subcutaneously. In some embodiments, the pharmaceutical composition is administered to the patients for an introduction regimen. In some optimized embodiments, the introduction regimen includes continuous administration of the pharmaceutical composition for at least 3, 5, 7 or 10 days. In some better embodiments, the pharmaceutical composition is administered to the patients for a maintenance regimen for at least 6 months after the introduction. In some better embodiments, the maintenance regimen includes an administration of the pharmaceutical composition every 3, 5, 7 or 10 days.

In a third aspect, the present invention provides a pharmaceutical composition comprise an effective amount of neuregulin for preventing, treating or delaying cardiac complications in diabetic patients. In some embodiments, the cardiac complication is heart failure. In some embodiments, the benefit is significant reduction of mortality rate. In some embodiments, the benefit is significant reduction of rehospitalization. In some embodiments, the benefit is the improvement of the biomarkers levels which indicate the improvement of chronic heart failure. In some embodiments, the cardiac complication is heart failure.

In a fourth aspect, the present invention provides a combination, which comprises an effective amount of neuregulin and an effective amount of a prophylactic or therapeutic agents for diabetic mellitus.

In a fifth aspect, the present invention provides a method to improve survival or reduce mortality of chronic heart failure patients, comprising administering a pharmaceutical composition comprising an effective amount of neuregulin to the chronic heart failure patients. In one embodiment, chronic heart failure patients are diabetic patients. In some embodiments, the pharmaceutical composition is administered to the patients intravenously or subcutaneously. In some embodiments, the pharmaceutical composition is administered to the patients for an introduction regimen. In some optimized embodiments, the introduction regimen includes continuous administration of the pharmaceutical composition for at least 3, 5, 7 or 10 days. In some better embodiments, the pharmaceutical composition is administered to the patients for a maintenance regimen for at least 6 months after the introduction. In some better embodiments, the maintenance regimen includes an administration of the pharmaceutical composition every 3, 5, 7 or 10 days.

In a sixth aspect of the invention, the use of neuregulin protein for preparation of a medication was provided. The medication can be provided to chronic heart failure patients for long-term benefits. In some embodiments, the chronic heart failure patients are diabetic patients. In some embodiments, the long-term benefit is the improvement of survival. In some embodiments, the long-term benefit is the reduction of re-hospitalization. In another embodiment, the long-term benefit is the improvement of biomarkers which indicate the long-term prognosis of chronic heart failure.

DETAILED DESCRIPTION OF THE INVENTION

For clarity of disclosure, and not by way of limitation, the detailed description of the invention hereinafter is divided into the subsections that follow. All publications mentioned herein are incorporated by reference to disclose and describe the methods and/or materials in connection with which the publications are cited.

Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a", "an", and "the" mean "at least one" or "one or more" unless the context clearly dictates otherwise.

As used herein, "neuregulin" or "NRG" used in the present invention refers to proteins or peptides that can bind and activate ErbB2, ErbB3, ErbB4 or combinations thereof, including but not limited to all neuregulin isoforms, neuregulin EGF-like domain alone, polypeptides comprising neuregulin EGF-like domain, neuregulin mutants or derivatives, and any kind of neuregulin-like gene products that also activate the above receptors as described in detail below. Neuregulin also includes NRG-1, NRG-2, NRG-3 and NRG-4 proteins, peptides, fragments and compounds that mimic the activities of neuregulin. Neuregulin used in the present invention can activate the above ErbB receptors and modulate their biological reactions, e.g., stimulate acetylcholine receptor synthesis in skeletal muscle cell; and/or improve cardiocyte differentiation, survival and DNA synthesis. Neuregulin also includes those variants with conservative amino acid substitutions that do not substantially alter their biological activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al., Molecular Biology of the Gene, 4$^{th}$ Edition, 1987, The Bejacmin/Cummings Pub.co., p. 224). In preferred embodiments, neuregulin used in the present invention binds to and activates ErbB2/ErbB4 or ErbB2/ErbB3 heterodimers, for example, but not for the purpose of restriction, peptides including the 177-237 residues of NRG-1 β2 isoform containing the amino acid sequence: SHLVKCAEKEKTFCVNGGECF MVKDLSNPSRYLCKCPNEFTGDRCQNYVMASFY-KAEELYQ (SEQ ID NO:1). The peptides including the 177-237 residues of NRG-1 β2 isoform comprises the EGF-like domian, which has been proved to be sufficient to bind to and activate the receptors.

As used herein, "epidermal growth factor-like domain" or "EGF-like domain" refers to a polypeptide motif encoded by the neuregulin gene that binds to and activates ErbB2, ErbB3, ErbB4, or combinations thereof, and bears a structural similarity to the EGF receptor-binding domain as disclosed in WO 00/64400, Holmes et al., Science, 256: 1205-1210 (1992); U.S. Pat. Nos. 5,530,109 and 5,716,930; Hijazi et al., Int. J. Oncol., 13:1061-1067 (1998); Chang et al., Nature, 387:509-512 (1997); Carraway et al., Nature, 387:512-516 (1997); Higashiyama et al., J. Biochem., 122: 675-680 (1997); and WO 97/09425, the contents of which are all incorporated herein by reference. In certain embodiments, EGF-like domain binds to and activates ErbB2/ErbB4 or ErbB2/ErbB3 heterodimers. In certain embodiments, EGF-like domain comprises the amino acid sequence of the receptor binding domain of NRG-1. In some embodiments, EGF-like domain comprises the amino acid sequence corresponding to amino acid residues 177-226, 177-237, or 177-240 of NRG-1. In certain embodiments, EGF-like domain comprises the amino acid sequence of the receptor binding domain of NRG-2. In certain embodiments, EGF-like domain comprises the amino acid sequence of the receptor binding domain of NRG-3. In certain embodiments, EGF-like domain comprises the amino acid sequence of the receptor binding domain of NRG-4. In certain embodiments, EGF-like domain comprises the amino acid sequence of Ala Glu Lys Glu Lys Thr Phe Cys Val Asn Gly Gly Glu Cys Phe Met Val Lys Asp Leu Ser Asn Pro, as described in U.S. Pat. No. 5,834,229.

The formulation, dosage and route of administration of a neuregulin protein, preferably in the form of pharmaceutical compositions, can be determined according to the methods known in the art (see e.g., Remington: The Science and Practice of Pharmacy, Alfonso R. Gennaro (Editor) Mack Publishing Company, April 1997; Therapeutic Peptides and Proteins: Formulation, Processing, and Delivery Systems, Banga, 1999; and Pharmaceutical Formulation Development of Peptides and Proteins, Hovgaard and Frkjr (Ed.), Taylor & Francis, Inc., 2000; Medical Applications of Liposomes, Lasic and Papahadjopoulos (Ed.), Elsevier Science, 1998; Textbook of Gene Therapy, Jain, Hogrefe & Huber Publishers, 1998; Adenoviruses: Basic Biology to Gene Therapy, Vol. 15, Seth, Landes Bioscience, 1999; Biopharmaceutical Drug Design and Development, Wu-Pong and Rojanasakul (Ed.), Humana Press, 1999; Therapeutic Angiogenesis: From Basic Science to the Clinic, Vol. 28, Dole et al. (Ed.), Springer-Verlag New York, 1999).

The neuregulin protein, can be formulated for oral, rectal, topical, inhalational, buccal (e.g., sublingual), parenteral (e.g., subcutaneous, intramuscular, intradermal, or intravenous), transdemal administration or any other suitable route of administration. The most suitable route in any given case will depend on the nature and severity of the condition being treated and on the nature of the particular neuregulin protein, which is being used. The neuregulin proteincan be administered alone. Alternatively and preferably, the neuregulin protein is co-administered with a pharmaceutically acceptable carrier or excipient. Any suitable pharmaceutically acceptable carrier or excipient can be used in the present method (See e.g., Remington: The Science and Practice of Pharmacy, Alfonso R. Gennaro (Editor) Mack Publishing Company, April 1997).

According to the present invention, the neuregulin protein, alone or in combination with other agents, carriers or excipients, may be formulated for any suitable administration route, such as intracavernous injection, subcutaneous injection, intravenous injection, intramuscular injection, intradermal injection, oral or topical administration. The method may employ formulations for injectable administration in unit dosage form, in ampoules or in multidose containers, with an added preservative. The formulations may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, sterile pyrogen-free water or other solvents, before use. Topical administration in the present invention may employ the use of a foam, gel, cream, ointment, transdermal patch, or paste.

Pharmaceutically acceptable compositions and methods for their administration that may be employed for use in this invention include, but are not limited to those described in U.S. Pat. Nos. 5,736,154; 6,197,801 B1; 5,741,511; 5,886,039; 5,941,868; 6,258,374 B1; and 5,686,102.

The magnitude of a therapeutic dose in the treatment or prevention will vary with the severity of the condition to be treated and the route of administration. The dose, and perhaps dose frequency, will also vary according to age, body weight, condition and response of the individual patient.

It should be noted that the attending physician would know how to and when to terminate, interrupt or adjust therapy to lower dosage due to toxicity, or adverse effects. Conversely, the physician would also know how to and when to adjust treatment to higher levels if the clinical response is not adequate (precluding toxic side effects).

Any suitable route of administration may be used. Dosage forms include tablets, troches, cachet, dispersions, suspensions, solutions, capsules, patches, and the like. See, Remington's Pharmaceutical Sciences. In practical use, the neuregulin protein, alone or in combination with other agents, may be combined as the active in intimate admixture with a pharmaceutical carrier or excipient, such as beta-cyclodextrin and 2-hydroxy-propyl-beta-cyclodextrin, according to conventional pharmaceutical compounding techniques. The carrier may take a wide form of preparation desired for administration, topical or parenteral. In preparing compositions for parenteral dosage form, such as intravenous injection or infusion, similar pharmaceutical media may be employed, water, glycols, oils, buffers, sugar, preservatives, liposomes, and the like known to those of skill in the art. Examples of such parenteral compositions include, but are not limited to dextrose 5% w/v, normal saline or other solutions. The total dose of the neuregulin protein, alone or in combination with other agents to be administered may be administered in a vial of intravenous fluid, ranging from about 1 ml to 2000 ml. The volume of dilution fluid will vary according to the total dose administered.

The invention also provides for kits for carrying out the therapeutic regimens of the invention. Such kits comprise in one or more containers therapeutically effective amounts of the neuregulin protein, alone or in combination with other agents, in pharmaceutically acceptable form. Preferred pharmaceutical forms would be in combination with sterile saline, dextrose solution, or buffered solution, or other pharmaceutically acceptable sterile fluid. Alternatively, the composition may be lyophilized or dessicated; in this instance, the kit optionally further comprises in a container a pharmaceutically acceptable solution, preferably sterile, to reconstitute the complex to form a solution for injection purposes. Exemplary pharmaceutically acceptable solutions are saline and dextrose solution.

In another embodiment, a kit of the invention further comprises a needle or syringe, preferably packaged in sterile form, for injecting the composition, and/or a packaged alcohol pad. Instructions are optionally included for administration of composition by a physician or by the patient.

As used herein, "treat", "treatment" and "treating" refer to any manner in which the symptoms of a condition, disorder or disease are ameliorated or otherwise beneficially altered. The effect may be prophylactic in terms of completely or partially preventing a disease or symptom thereof and/or may be therapeutic in terms of a partial or complete cure for a disease and/or adverse effect attributable to the disease. Treatment also encompasses any pharmaceutical use of the compositions herein.

As used herein, "heart failure" means an abnormality of cardiac function where the heart does not pump blood at the rate needed for the requirements of metabolizing tissues. Heart failure includes a wide range of disease states such as congestive heart failure, myocardial infarction, tachyarrhythmia, familial hypertrophic cardiomyopathy, ischemic heart disease, idiopathic dilated cardiomyopathy, myocarditis and the like. The heart failure can be caused by any number of factors, including, without limitation, ischemic, congenital, rheumatic, viral, toxic or idiopathic forms. Chronic cardiac hypertrophy is a significantly diseased state which is a precursor to congestive heart failure and cardiac arrest.

As used herein, "protein" is synonymous with "polypeptide" or "peptide" unless the context clearly dictates otherwise.

As used herein, "plasma" is synonymous with "serum" unless the context clearly dictates otherwise.

As used herein, "long-term benefit" means benefit caused by a treatment or interference which may not be observed in a short period after the treatment or interference. For chronic heart failure patients, long-term benefit may be improvement of survival, reduction of re-hospitalization or improvement of biomarkers which indicate the long-term prognosis. In some embodiments, the time period for observation of the benefit is about 6 months. In some embodiments, the time period for observation of the benefit is about 1 year. In some embodiments, the time period for observation of the benefit is about 2 years. And in other embodiments, the time period for observation of the benefit is about 3 years, 5 years, 10 years or longer.

As used herein, "survival" means the time or probability one subject may remain alive or living. It could be expressed by survival time or survival rate. Survival time is the time period start from the diagnosis or treatment to the end of the life. Survival rate means the percentage of people who are alive for a given period of time after diagnosis or treatment. For each subject, prolonged survival time caused by a treatment or interference could be regarded as a benefit. For a group of subjects or large populations, prolonged mean survival time or increased survival rate could be regarded as a benefit.

As used herein, "re-hospitalization" means the times or frequency of the patient admitted to the hospital in a given period of time. The admission to the hospital may be caused by all conditions, or only caused by the same condition which is being treated. For each subject, a reduction of times of re-hospitalizations in a given period of time could be regarded as a benefit. And for a group of subjects or large populations, a reduction of total times or mean times of re-hospitalizations could be regarded as a benefit.

BNP and NT-proBNP plasma levels are promising tools in the daily management of suspected or established heart failure. Most studies on the use of BNP and NT-proBNP in clinical practice addressed their diagnostic properties, and an increasingly amount of evidence is available supporting the prognostic value of BNP and NT-proBNP. As NT-proBNP has about 6 times longer of half-life in the blood than BNP, it is more widely used as a diagnostic or prognostic marker for heart failure. The plasma NT-proBNP level can be analyzed by commercial kits. For the purpose of example, but not limitation, the commercial kits from Roche or Biomedica. In the examples of the present invention, the NT-proBNP level was detected by kit from Biomedica (Austria).

Both BNP and NT-proBNP levels in the blood are used for screening, diagnosis of heart failure and are useful to establish prognosis in heart failure, as both markers are typically higher in patients with worse outcome. And, it is discovered in the present invention that plasma level of BNP or NT-proBNP is indicative of the patient being suitable for heart failure treatment by neuregulin. In fact, any diagnostic or prognostic markers for heart failure can be used to determine whether a patient is suitable for heart failure treatment by neuregulin. The plasma level of NT-proBNP identified in this invention shall be used as guidance rather than a limitation for selection of heart failure patients who will receive significant treatment benefits from neuregulin. For example, using a plasma level of 5000 fmol/ml is still able to select heart failure patients who will receive treatment benefits from neuregulin, but some of these patients will receive treatment benefits in a lesser degree.

As used herein, "activity unit" or "EU" or "U" means the quantity of standard product that can induce 50% maximal reaction. In other words, to determine the activity unit for a given active agent, the EC50 must be measured. For example, if the EC50 for a batch of product was 0.1 µg, then that would be one unit. Further, if 1 µg of that products is being used, then 10 EU (1/0.1) is being used. The EC50 can be determined by any method known in the art, including the method employed by the inventors. This determination of the activity unit is important for quality control of genetically engineered products and clinically used drugs, permits product from different pharmaceuticals and/or different batch numbers to be quantified with uniform criteria.

The following is an exemplary, rapid, sensitive, high flux and quantitative method for determination of biological activity of NRG-1 through combining NRG with cell surface ErbB3/ErbB4 molecule and indirect mediation of ErbB2 phosphorylation (See e.g., Michael D. Sadick et al., 1996, Analytical Biochemistry, 235:207-214 and WO03/099300).

Briefly, the assay, termed a kinase receptor activation enzyme-linked immunosorbant assay (KIRA-ELISA), consists of two separate microtiter plates, one for cell culture, ligand stimulation, and cell lysis/receptor solubilization and the other plate for receptor capture and phosphotyrosine ELISA. The assay was developed for analysis of NRG-induced ErbB2 activation and utilizes the stimulation of intact receptor on the adherent breast carcinoma cell line, MCF-7. Membrane proteins are solubilized via Triton X-100 lysis and the receptor is captured in ELISA wells coated with ErbB2-specific antibodies with no cross-reaction to ErbB3 or ErbB4. The degree of receptor phosphorylation is then quantified by antiphosphotyrosine ELISA. A reproducible standard curve is generated with a EC50 of approximately 360 pM for heregulin beta 1 (177-244). When identical samples of HRG beta 1 (177-244) are analyzed by both the KIRA-ELISA and quantitative antiphosphotyrosine Western Blot analysis, the results correlate very closely with one another. The assay described in this report is able to specifically quantify tyrosine phosphorylation of ErbB2 that results from the interaction of HRG with ErbB3 and/or ErbB4.

Since most of the genetically engineered medicines are proteins and polypeptides, their activity can be determined by their amino acid sequences or the activity center formed by their spatial structure. Activity titer of protein and polypeptide is not consistent with their absolute quality, therefore cannot be determined with weight unit as that of chemical drugs. However, biological activity of genetically engineered medicines is generally consistent with their pharmacodynamics and titer determination system established through given biological activity can determine its titer unit. Therefore, biological activity determination can be part of a process of titering the substance with biological activity and is an important component of quality control of genetically engineered product. It is important to determine biological activity criteria for quality control of genetically engineered product and clinically used drugs.

Quantity of standard product that can induce 50% maximal reaction is defined as an activity unit (1 EU). Accordingly, product from different pharmaceuticals and of different batch numbers can be quantified with uniform criteria.

EXAMPLES

Example 1

The Effect of Neucardin™ Administration by Different Routes on the Survival Rate of Rats with CHF Introduction In this study, we used a coronary artery ligation (CAL) model mimicking the myocardial infarction in the diabetic patients to investigate whether administration of Neucardin™ by IV drip using a by micro-injection pump or by subcutaneous (SC) bolus had any effects on survival rate and cardiac hemodynamics, 120 days after the initiation of administration of Neucardin™ 4 weeks after CAL. Echocardiography and cardiac remodeling were also used to determine cardiac function and recovery from CAL.

2. Methods:

2.1. Test Animals:

Strain, Origin: Wistar rats, Shanghai SLAC Laboratory Animal CO. LTD; Weight, 200±10 g, male;

2.2 Test Article:

2.2.1 Neucardin™

Identification: Recombinant human neuregulin-1 for injection (rhNRG-1, Neucardin™)

Lot Number: 200607009

Manufacturer: Zensun (Shanghai) Sci & Tech Co., Ltd

Dose form: Lyophilized powder

Appearance: White or off-white cake

Labeled Content of rhNRG-1: 250 µg/vial

Specific activity: 4897 U/vial

Storage conditions: 2-8° C.

2.2.2 Vehicle:

Identification: Placebo for recombinant human neuregulin-1

Dose form: Lyophilized powder
Appearance: White or off-white cake
Composition: Human serum albumin, mannitol, phosphate, NaCl
Storage conditions: 2~8° C.

2.3 Procedure:

2.3.1 to Establish the Rat CHF Model:

The LAD of the rats was ligated. Briefly, the rats were anesthetized with ketamine hydrochloride (100 mg/kg, IP) and their chest was shaved and sterilized. The rats were endotracheally intubated and mechanically ventilated with room air (respiratory rate 60 breaths/min, tidal volume 20 ml). A left thoracotomy was then performed at the 4th and 5th intercostal space and then the skin was incised along the left sternal border. The fourth rib was then cut proximal to the sternum. The pericardial sac was perforated and the heart was exposed. The LAD was ligated approximately 2 mm from its origin using a 6-0 silk suture. Subsequently, the air within the thorax was removed and the chest was closed in three layers (ribs, muscles and then skin). The rats were then allowed to resume spontaneous respiration, recover from the anesthesia and were then returned to their cages. Rats were maintained during a period of 4 weeks, then echocardiography evaluated, included in the formal study if they were shown an EF % value of 30-45%. Animals from all Groups were housed 5 per cage, fed ad libitum with standard diet and had free access to pure water. Room temperature was maintained at 21±1° C. and in a 12 h light/dark cycle.

2.3.2 IV Drip Via Microinjection Pump:

The method of IV drip of vehicle or Neucardin™ was through the tail vein. For this procedure, an appropriate rat restrainer was used according to the weight of the animal. The rat was placed near the restrainer and was gently placed into the apparatus. Normally the rats entered the restrainer without aid. Subsequently the tail of the rat was swabbed with a gauze dampened with alcohol to increase blood flow to the tail vein and to the intenerate skin corneum. The two lateral (on the side) tail veins were located and with the bevel of the needle facing upward with the needle almost parallel to the vein, the needle was inserted 2 mm into the tail vein 2-3 cm from the end of the tail. To confirm that the needle was successfully inserted into the tail vein, blood was extracted into the hub of the needle. The needle was fixed into the tail using medical tape. The infusion of drug or vehicle at the appropriate rate (0.2-0.4 ml/h) by microinjection pump or bolus injection was initiated.

2.3.3 SC Bolus

The SC bolus of vehicle or Neucardin™ was from the back of the rat. For this procedure, an appropriate rat restrainer was used according to the weight of the animal. The back of the rat was swabbed with gauze dampened with alcohol to sterilize the skin. With the bevel of the needle facing upward with the needle almost parallel to the skin, the needle was subcutaneously inserted 3-4 cm into the back of the rat. The needle was fixed onto the back using medical tape and connected to the perfusion tube. Then, the rat was placed near the restrainer and was gently placed into the apparatus. Normally the rats entered the restrainer with no aid. After fasten the restrainer, the bolus injection was initiated.

2.3.4 Experiment Groups and Drug Infusion:

MI rats were randomized by EF % value into four Groups as follows:

Group A (Negative control) for both IV and SC bolus. n=58 rats: IV drip of vehicle for 10-days by micro-injection pump at a speed of 0.2 ml/h for 8 h each day for the first 10 days, SC bolus of vehicle (same volume as Neucardin™), every 5 days until Day 120;

Group B (SC bolus Neucardin™), n=58: IV drip of vehicle by micro-injection pump at a speed of 0.2 ml/h for 8 h each day in the first 10 days, SC bolus Neucardin™ (10 μg/day), every 5 days until Day 120;

Group C (IV drip Neucardin™), n=57: IV drip of Neucardin™ (0.625 μg/kg/h) by micro-injection pump at a speed of 0.2 ml/h for 8 h each day for the first 10 days, SC bolus of vehicle (same volume as Neucardin™), every 5 days until Day 120.

Group D (IV drip and SC bolus Neucardin™), n=57: IV drip of Neucardin™ (0.625 μg/kg/h) by micro-injection pump at a rate of 0.2 ml/h for 8 h per day for the first 10 days, SC bolus of vehicle (same volume as Neucardin™) at 1st, 6th, 11th day, and then SC bolus Neucardin™ (10 μg/kg), every 5 days from 16th day to the end.

2.3.5 Data Acquisition

Survival rate; Echocardiography parameters; Hemodynamics parameters;

3. Results 3.1 Survival Rate:

Table 1 illustrates the survival rates between each Group. The survival rates were 48.3%, 62.1%, 64.9% and 82.5% in the IV drip & SC bolus of vehicle Group A, SC bolus of Neucardin™ Group B, IV drip of Neucardin™ Group C and IV drip & SC bolus of Neucardin™ Group D, respectively. All the survival rate or mean survival time of mortalities in Group B, C and D were improved or prolonged compared to Group A with Group D had best efficacy.

TABLE 1

Mortality, Survival rate and Mean survival time in the four Groups

| Group | Treatment | Start rat number | Deaths | Survival rat number | Survival rate (%) | Mean survival time of mortalities in days ± S.E. |
|---|---|---|---|---|---|---|
| A | Vehicle | 58 | 30 | 28 | 48.3% | 83.8 ± 5.9 |
| B | SC bolus Neucardin ™ | 58 | 22 | 36 | 62.1% | 91.4 ± 5.5 |
| C | IV drip Neucardin ™ | 57 | 20 | 37 | 64.9% | 97.5 ± 5.1 |
| D | SC bolus & IV drip Neucardin ™ | 57 | 10 | 47 | 82.5% | 107.5 ± 4.1 |

3.2 Echocardiography Parameters:

Echocardiography parameters were shown in Table 2. Four-weeks after coronary artery ligation and before administration of the test article, the CHF rats were randomized into four Groups according to their EF % values. As shown in Table 2, there were no significant differences between the four Groups before treatment (BT). 120 days after the start of administration, the EF % values were 30.7±3.1, 32.9±4.1, 33.5±3.4, 36.2±4.8% in the vehicle, Neucardin™ via SC bolus, Neucardin™ via IV drip and Neucardin™ via IV drip plus SC bolus Groups, respectively. After treatment, EF % and FS % of Group B, C and D were all higher than that of Group A.

4. Conclusion

A combined administration of Neucardin™ by IV drip & SC bolus or administration of the peptide given by each route alone all increased the survival rate of rats with CHF induced by CAL and improved cardiac functional parameters compared to rats treated with vehicle.

TABLE 2

Echocardiography parameters in the four Groups

| Group | BT AT | N | LVEDd (cm) | LVEDs (cm) | EF % (%) | FS % (%) |
|---|---|---|---|---|---|---|
| A. Negative control | BT | 58 | 0.987 ± 0.083 | 0.829 ± 0.088 | 38.0 ± 5.5 | 16.2 ± 2.7 |
|  | AT | 25 | 1.100 ± 0.089 | 0.961 ± 0.090 | 30.7 ± 3.1 | 12.7 ± 1.4 |
| B. SC bolus Neucardin ™ | BT | 58 | 0.992 ± 0.066 | 0.831 ± 0.066 | 38.2 ± 4.0 | 16.3 ± 2.0 |
|  | AT | 33 | 1.104 ± 0.063 | 0.952 ± 0.070 | 33.1 ± 4.1 | 13.9 ± 1.9 |
| C. IV drip Neucardin ™ | BT | 57 | 0.985 ± 0.061 | 0.824 ± 0.068 | 38.5 ± 4.4 | 16.3 ± 2.1 |
|  | AT | 36 | 1.080 ± 0.072 | 0.929 ± 0.073 | 33.4 ± 3.4 | 14.0 ± 1.6 |
| D. SC bolus & IV drip Neucardin ™ | BT | 57 | 0.979 ± 0.065 | 0.818 ± 0.066 | 38.7 ± 4.3 | 16.5 ± 2.1 |
|  | AT | 44 | 1.052 ± 0.087 | 0.893 ± 0.092 | 36.2 ± 4.8 | 15.3 ± 2.4 |

BT: Before treatment;
AT: After treatment;

3.3 Hemodynamic Parameters:

Table 3 shows the MAP, HR, ±dp/dt, LVEDP and LVSP values as measured in the four Groups of anesthetized animals on day 121. When Neucardin™ was administered by SC bolus or by IV drip alone (Group B and C), Neucardin™ significantly increased dp/dt and −dp/dt by 19.6% and 27.1%, 22.5% and 29.8% compared to Group A. When Neucardin™ was administered by both IV drip and SC bolus routes (Group D), significant increases in mean arterial pressure (MAP, 112.3±5.5 mmHg), left ventricular systolic pressure (LVSP, 139.4±9.8 mmHg), +dp/dt (7012.1±903.0 mmHg/s), −dp/dt (−4353.2±847.6 mmHg/s) compared to vehicle were obtained. Interestingly, these values of MAP, LVSP, +dp/dt and −dp/dt were 10.6%, 9.2%, 38.5% and 37.8% higher than vehicle treated rats, respectively. The results showed that Group B, C and D were all better than Group A in hemodynamic parameters with Group D had best efficacy.

Example 2

A Randomized, Double-Blinded, Multi-Center, Placebo Controlled Study to Evaluate the Efficacy and Safety of Recombinant Human Neuregulin 1 in Patients with Chronic Heart Failure Based on Standard Treatment To evaluate the efficacy of recombinant human neuregulin-1 for injection on chronic heart failure including those diabetic patients with chronic heart failure, a phase II, double-blinded, multi-center, placebo controlled, standard treatment based study was carried out in multiple clinical centers in China. A total of 195 patients with NYHA Class II or III stable chronic heart failure including 21 diabetic patients were enrolled and randomized into three groups: placebo, or 0.6 µg/kg and 1.2 µg/kg of rhNRG-1. There were 13 patients with diabetic in Neucardin group (5 in 0.6

TABLE 3

Hemodynamics parameters in the four Groups

| Group | Treatment | N | SBP (mmHg) | DBP (mmHg) | MAP (mmHg) | LVSP (mmHg) |
|---|---|---|---|---|---|---|
| A | Vehicle | 14 | 118.7 ± 11.5 | 94.1 ± 12.3 | 102.3 ± 11.7 | 128.5 ± 14.7 |
| B | SC bolus Neucardin ™ | 27 | 123.8 ± 11.5 | 95.3 ± 8.9 | 104.9 ± 9.5 | 129.5 ± 13.6 |
| C | IV drip Neucardin ™ | 25 | 122.5 ± 10.5 | 95.0 ± 7.5 | 104.4 ± 8.2 | 131.7 ± 10.0 |
| D | SC bolus & IV drip Neucardin ™ | 35 | 132.6 ± 7.1 | 102.1 ± 5.3 | 112.3 ± 5.5 | 139.4 ± 9.8 |

| Group | Treatment | N | LVEDP (mmHg) | dp/dt (mmHg/s) | (−dp/dt) (mmHg/s) | Heart rate (Beat/min) |
|---|---|---|---|---|---|---|
| A | Vehicle | 14 | 5.8 ± 3.5 | 4995.6 ± 532.2 | 3087.5 ± 715.7 | 297.2 ± 16.0 |
| B | SC bolus Neucardin ™ | 27 | 4.5 ± 2.8 | 6050.9 ± 1231.3 | 4013.8 ± 838.3 | 292.6 ± 23.0 |
| C | IV drip Neucardin ™ | 25 | 4.0 ± 3.2 | 6199.9 ± 709.5 | 4098.9 ± 823.5 | 296.3 ± 13.5 |
| D | SC bolus & IV drip Neucardin ™ | 35 | 3.9 ± 2.5 | 7012.1 ± 903.0 | 4353.2 ± 847.6 | 292.5 ± 19.1 |

μg/kg/day arm and 8 in 1.2 μg/kg/day arm), and 9 patients in placebo group. There were no significant variations in demographics or background therapies among groups. According to the schedule, patients were administered the drug for 10 consecutive days in the hospital first, after finishing the day 11 follow up, they were discharged from the hospital. Another two on site follow up were at day 30 and day 90. A telephone interview was conducted one year after the last patient enrolled.

Investigational Product:

Specification: Neucardin™, 61 amino acid polypeptide comprises the EGF-like domain of Neuregulin-1 β2 isoform, with the molecular weight of 7054 Dal (1 μg=0.14 nmol). 250 μg (5000 EU)/vial (1 μg=20 EU).

Preparation: For injection.

Mode of administration: Intravenously drip.

Storage: in safe place, with limited access and protected from light, at 3-8° C.

Placebo:

Specification: Excipient for Neucardin™. 250 μg/vial and without active recombinant human neuregulin-1 protein.

Dosage Groups:

| | Dosage | | |
|---|---|---|---|
| | 0 μg/kg/day | 0.6 μg/kg/day | 1.2 μg/kg/day |
| Administration | Intravenous infusion | | |
| Volume | 50 ml | | |
| Course | 10 hours per day, for consecutive 10 days | | |

Study Procedure

Patients were randomly assigned to three groups, treated with placebo or rhNRG-1 (0.6 or 1.2 μg/kg/day) for 10 consecutive days, after finishing the day 11 follow up, they were discharged from the hospital. Another two on site follow up were at day 30 and day 90. Blood samples of each patient were collected before treatment and at day 11, 30 and 90. Plasma NT-proBNP was tested in the core lab with NT-proBNP assays (kit from Biomedica).

Figure 1:
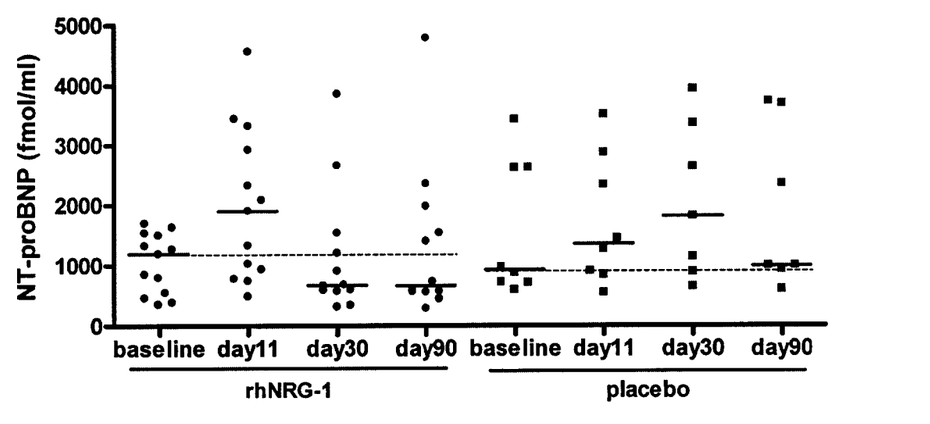
FIG. 1: The results of NT-proBNP in diabetic patients with rhNRG-1 and placebo in day 11, day 30 and 90.

With regards to the diabetic patients (5 in 0.6 μg/kg/day arm and 8 in 1.2 μg/kg/day arm, and 9 in placebo group), as shown in FIG. 1, decreased NT-proBNP levels in Neucardin™ treated patients in day 30 and 90 were observed, indicating improved long-term prognosis. For the increased level in day 11, it was caused by direct release of BNP from cardiomyocytes by Neucardin™ stimulation, which has been confirmed in preclinical studies.

These results showed that rhNRG-1 treatment can reduce the plasma level of NT-proBNP, which may indicate rhNRG-1 can provide long-term benefits to diabetic patients with chronic heart failure.

Example 3

A Randomized, Double-Blinded, Multi-Center, Placebo Controlled Survival Study of Recombinant Human Neuregulin 1 in Patients with Chronic Heart Failure Based on Standard Treatment To evaluate the efficacy of recombinant human neuregulin-1 for injection on chronic heart failure including those diabetic patients with chronic heart failure, a phase II, double-blinded, multi-center, placebo controlled, standard treatment based study was carried out in multiple clinical centers in China. A total of 351 patients with NYHA Class III or IV stable chronic heart failure were enrolled and randomized into placebo group or rhNRG-1 group (0.6 μg/kg). 68 of 351 patients were diabetic patients, with 35 cases in placebo group, and 33 cases in Neucardin™ group. There were no significant variations in demographics or background therapies among groups. According to the schedule, patients were administered with the drug for 10 consecutive days in the hospital, after finishing the day 11 follow up, they were discharged from the hospital, and were administered with the drug once weekly from the $3^{rd}$ week till the $25^{th}$ week as out-patient. Blood samples of each patient were collected before treatment (baseline) and at each follow up. The survival information was collected at 52th week of the study.

Investigational Product:

Specification: Neucardin™, 61 amino acid polypeptide comprises the EGF-like domain of Neuregulin-1 β2 isoform, with the molecular weight of 7054 Dal (1 μg=0.14 nmol). 250 μg (5000 EU)/vial (1 μg=20 EU).

Preparation: For injection.

Mode of administration: Intravenously drip or infusion.

Storage: in safe place, with limited access and protected from light, at 3-8° C.

Placebo:

Specification: Excipient for Neucardin™. 250 μg/vial and without active recombinant human neuregulin-1 protein.

Dosage and Regimens:

| | Day 1-10 | Week 3-25 |
|---|---|---|
| Dose | 0.6 μg/kg/day rhNRG-1 or placebo | 0.8 μg/kg/day rhNRG-1 or placebo |
| Route | Intravenous drip | Intravenous infusion |
| regimen | 10 hours per day for 10 days | 10 minutes infusion weekly |

Regarding the diabetic patients, the all-cause mortality of the placebo group at 52 week is 20%, with 7 death in 35 patients, while the number is 9.1% in rhNRG-1 group, with 3 death in 33 patients completed the trial. So from the results we can find around 55% decrease of the mortality of rhNRG-1 administration compared with placebo group, even the placebo group were still maintain their previous standard treatment for chronic heart failure.

Results of this study showed rhNRG-1 could significantly lower the mortality of diabetic patients with cardiac complications especially HF.

What is claimed is:

1. A method of treating cardiac complications in a human diabetic patient, comprising administering a pharmaceutical composition comprising an effective amount of neuregulin to the patient, wherein the neuregulin comprises SEQ ID NO: 1.

2. The method of claim 1, wherein the cardiac complication is heart failure.

3. The method of claim 1, wherein the neuregulin is neuregulin-1, and wherein the neuregulin-1 comprises SEQ ID NO: 1.

4. The method of claim 1, wherein the neuregulin consists of SEQ ID NO: 1.

5. The method of claim 1, wherein the pharmaceutical composition is administered to the patient intravenously or subcutaneously.

6. The method of claim 1, wherein the pharmaceutical composition is administered to the patient for an introduction regimen.

7. The method of claim 6, wherein the introduction regimen includes continuous administration of the pharmaceutical composition for at least 3, 5, 7 or 10 days.

8. The method of claim 6, wherein the pharmaceutical composition is administered to the patient for a maintenance regimen after the introduction regimen.

9. The method of claim 8, wherein the maintenance regimen includes an administration of the pharmaceutical composition every 3, 5, 7 or 10 days.

* * * * *